United States Patent
Nagamune et al.

(10) Patent No.: US 7,595,202 B2
(45) Date of Patent: Sep. 29, 2009

(54) ANALYSIS METHOD USING REPORTER (LABEL) INTERMOLECULAR INTERACTION

(75) Inventors: Teruyuki Nagamune, 2-2-10-306, Yoshida-shinmachi 1-chome, Kawagoe-shi, Saitama 350-0808 (JP); Hiroshi Ueda, Kiyose (JP); Yoshiyuki Ohiro, Shimotsuga-gun (JP); Norio Shibata, Shimotsuga-gun (JP)

(73) Assignees: Teruyuki Nagamune, Saitama (JP); Eiken Nagaku Kabushiki Kaisha, Tokyo (JP)

( * ) Notice: Subject to any disclaimer, the term of this patent is extended or adjusted under 35 U.S.C. 154(b) by 862 days.

(21) Appl. No.: 10/475,540

(22) PCT Filed: Apr. 23, 2002

(86) PCT No.: PCT/JP02/04022

§ 371 (c)(1), (2), (4) Date: Oct. 20, 2003

(87) PCT Pub. No.: WO02/088733

PCT Pub. Date: Nov. 7, 2002

(65) Prior Publication Data
US 2004/0110245 A1 Jun. 10, 2004

(30) Foreign Application Priority Data
Apr. 23, 2001 (JP) .............................. 2001-123866

(51) Int. Cl.
- *G01N 33/541* (2006.01)
- *G01N 21/76* (2006.01)
- *G01N 33/533* (2006.01)
- *G01N 33/566* (2006.01)
- *G01N 33/53* (2006.01)
- *G01N 33/542* (2006.01)

(52) U.S. Cl. ............... 436/540; 436/172; 436/546; 436/501; 435/7.1; 435/7.9; 435/7.91; 422/61

(58) Field of Classification Search .................. None
See application file for complete search history.

(56) References Cited

U.S. PATENT DOCUMENTS

| 5,470,952 A | * | 11/1995 | Stahl et al. .................. 530/350 |
| 5,643,731 A | * | 7/1997 | Bosslet et al. ................ 435/7.1 |
| 2002/0064779 A1 | * | 5/2002 | Landegren et al. ............. 435/6 |

FOREIGN PATENT DOCUMENTS

| JP | A 4-301570 | 10/1992 |
| JP | A 10-078436 | 3/1998 |
| JP | A 10-319017 | 12/1998 |

(Continued)

OTHER PUBLICATIONS

Kohler et al. "Kinetic studies of Fos.Jun.DNA complex formation: DNA binding prior to dimerization" Biochemistry Jan. 9, 2001;40(1):130-42.*

(Continued)

*Primary Examiner*—Christopher L Chin
*Assistant Examiner*—Christine Foster
(74) *Attorney, Agent, or Firm*—Peter F. Corless; Christine C. O'Day; Edwards Angell Palmer & Dodge LLP

(57) ABSTRACT

The present invention provides a method for controlling the spatial arrangement of an energy donor and an energy acceptor in a reaction complex in order to carry out the measurement with good precision and high sensitivity, and a measurement system using the method. Two types of material having affinity for the subject material to be measured are respectively labeled with a combination of reporters that give rise to energy transfer; those that have been thus obtained by labeling these materials are each further labeled with materials that have weak affinity for each other to give reagents, which are then mixed with a sample to give the reaction complex. Each of the materials is brought into spatial proximity by binding based on the affinity among the materials having weak affinity for each other in the reaction complex, and since that condition is stably maintained, a more efficient energy transfer occurs.

6 Claims, 3 Drawing Sheets

FOREIGN PATENT DOCUMENTS

| | | |
|---|---|---|
| JP | A 2001-124770 | 5/2001 |
| JP | A 2001-525187 | 12/2001 |
| WO | WO 98/15830 | 4/1998 |
| WO | WO 99/28746 | 6/1999 |
| WO | WO 01/61037 A1 | 8/2001 |

OTHER PUBLICATIONS

R. Ballerstadt et al., *Analytica Chimica Acta*, vol. 345, pp. 203-212 (1997).

A. Kenworthy, *Methods*, vol. 24, pp. 289-296 (2001).

P. Wu et al., *Anal. Biochem.*, vol. 218, pp. 1-13 (1994).

R. Arai et al., *Anal. Biochem.*, vol. 289, pp. 77-81 (2001).

F. Rossi et al., *Proc. Natl. Acad. Sci. USA*, vol. 94, pp. 8405-8410 (1997).

C. Suzuki et al., *J. Biochem*, vol. 122, pp. 322-329 (1997).

\* cited by examiner

ANALYSIS METHOD USING REPORTER (LABEL) INTERMOLECULAR INTERACTION

TECHNICAL FIELD

The present invention relates to a method of analyzing materials by means of interaction between reporters. In particular, it relates to a high sensitivity analytical method in which the interaction between reporters increases as the reporters are brought in proximity to each other.

BACKGROUND ART

Intensive research has been carried out into, for example, increasing the sensitivity and simplifying the measurement systems for the analysis and measurement of specific materials in various fields such as clinical diagnosis, food hygiene, and environmental hygiene. In particular, immunoassays employing an antigen-antibody reaction are more widely employed thereamong, for reasons of sensitivity and specificity. The sandwich enzyme immunoassay (EIA) method can be cited as a representative immunoassay method.

In sandwich EIA, of two types of antibody for a subject material to be measured, one is immobilized on a solid phase; this solid phase, the other antibody which is labeled with an enzyme, and a test sample are mixed together and reacted; after removing unreacted enzyme-labeled antibody by washing, an enzyme substrate solution is added and the amount of immunocomplex generated is measured by the enzyme activity. Since this method has good reproducibility and, furthermore, the antigen concentration can be measured with high sensitivity, it is widely employed. However, the sandwich method has the problem that a complicated and time-consuming washing operation for removing unreacted labeled antibody is necessary, etc.

In order to solve this problem, in recent years immunoassay methods employing energy transfer phenomena such as fluorescence energy transfer (FRET), bioluminescence energy transfer (BRET), and chemiluminescence energy transfer (CRET), or intermolecular interactions such as the complementation of enzyme activity of enzyme molecules of which a part has been deleted or altered have been noteworthy. Fluorescence energy transfer is a phenomenon observed between certain specific fluorescent materials; in a case where the fluorescence spectrum of a fluorescence energy donor and the excitation light spectrum of a fluorescence energy acceptor overlap and, moreover, where the distance between these two molecules approaches 10 nm or less, the fluorescence energy of the fluorescence energy donor transfers to the acceptor, and luminescence of the fluorescence energy acceptor is observed.

Bioluminescence energy transfer is a phenomenon observed between a fluorescent material and an enzyme, such as firefly luciferase, that catalyses bioluminescence; in a case where the luminescence spectrum of the bioluminescence enzyme and the excitation light spectrum of a luminescence energy acceptor overlap and, moreover, where the distance between these two molecules approaches 10 nm or less, the luminescence energy of the bioluminescence energy donor transfers to the acceptor, and fluorescence of the luminescence energy acceptor is observed.

Chemiluminescence energy transfer is a phenomenon observed between a fluorescent material and an enzyme, such as a peroxidase, that catalyses chemiluminescence; in a case where the luminescence spectrum of the chemiluminescence enzyme and the excitation light spectrum of a luminescence energy acceptor overlap and, moreover, where the distance between these two molecules approaches 10 nm or less, the luminescence energy of the chemiluminescence energy donor transfers to the acceptor, and fluorescence of the luminescence energy acceptor is observed.

The complementation of enzyme activity of enzyme molecules of which a part has been deleted or altered is a phenomenon typified by the β-galactosidase $\Delta\alpha$ mutant in which the α site has been deleted, and the $\Delta\omega$ mutant in which the ω site has been deleted; by themselves $\Delta\alpha$ and $\Delta\omega$ have reduced β-galactosidase enzyme activity, but when the two approach each other the β-galactosidase enzyme activity increases as a result of association. Several examples have been reported so far in which such energy transfer phenomena and such complementation of enzyme activity of enzyme molecules of which a part has been deleted or altered are applied to immunoassay and the detection of protein-protein interaction.

Among these, as an example of the application of the energy transfer phenomena to an immunoassay there can be cited a method reported by Toyobo Co., Ltd. (JP, A, 10-319017). In this method, materials A and B that have the capacity to bind to a subject material (X) to be measured are labeled with materials F1 and F2 respectively, which have a fluorescence energy donor-acceptor relationship; A-F1, X, and B-F2 are mixed and reacted for a fixed time, and after forming a complex F1-A:X:B-F2, without carrying out a washing operation, the amount of F1-A:X:B-F2 is measured as the efficiency of fluorescence energy transfer from F1 to F2.

However, the actual subject material to be immunoassayed (antigen) is often a high molecular weight protein and, furthermore, when two types of monoclonal antibody are used, etc., since the two epitopes are spatially separated, even if the reaction complex F1-A:X:B-F2 is formed, F1 and F2 in the F1-A:X:B-F2 complex are not in spatial proximity, and efficient energy transfer cannot take place. As a result, there is the problem that the sensitivity of the measurement is low.

According to Förster's theory of fluorescence energy transfer, the efficiency of fluorescence energy transfer is inversely proportional to the sixth power of the distance between the donor and acceptor (Anal. Biochem, 218, 1-13, 1994). Thus, when applying the FRET, BRET, CRET, etc. energy transfer phenomena to an immunoassay, it is necessary to establish a technique that always arranges the luminescence energy donor and acceptor in fixed positions within this type of immunocomplex.

In the application of FRET to immunoassay, the method of Ueda et al. (JP, A, 10-78436) can be cited as an example in which the spatial arrangement of the energy donor and acceptor is carried out well. In this method, antibody VL and VH fragments are labeled with fluorescence energy donor and acceptor and, in the presence of an antigen, fluorescence energy transfer takes place only when a stable three-way association of antigen, VL, and VH is formed, and by measuring the fluorescence intensity ratio of the fluorescence energy donor and acceptor, the antigen concentration is measured. It has been demonstrated (Anal. Biochem, 289, 77-81, 2001) that this measurement method employing VL and VH can measure the antigen concentration in BRET also.

This method, which combines, with fluorescence energy transfer, the property of VL and VH antibody fragments always being within 5 nm when an antigen is present, is an exceptionally unique immunoassay method, but since for many of the antibodies present in nature VL and VH have the property of associating even in the absence of an antigen, this principle cannot be applied to all antibodies. As a result, it cannot be put to practical use.

Furthermore, a method in which the complementation of enzyme activity of enzyme molecules of which a part has been deleted or altered was applied to monitoring protein-protein interaction has been reported by Rossi et al. (Proc. Natl. Acad. Sci. USA, 94, 8405-8410, 1997). In the method of Rossi et al., expression vectors of the proteins FRAP and FKBP12, for which dimerization is induced by rapamycin, fused with Δα and Δω β-galactosidases respectively were introduced into mammalian cells; when rapamycin was added to these chimeric protein-expressing cells, dimerization of the FRAP and FKBP12 proteins took place due to the rapamycin, and as a result rapamycin concentration-dependent β-galactosidase activity could be measured.

This method is an extremely good method for carrying out measurement of a material in viable cells, but it is an extremely special example in which the low molecular weight rapamycin-induced dimerization of FRAP and FKBP is utilized. When using this kind of enzyme complementation in the detection of an immunocomplex in immunoassay, in the same way as immunoassay methods employing energy transfer such as FRET, a technique that always arranges reporter proteins in fixed positions is also necessary.

Therefore, when intermolecular interactions such as an energy transfer phenomenon like fluorescence energy transfer (FRET) or luminescence-fluorescence energy transfer (BRET) and the complementation of enzyme activity of enzyme molecules of which a part has been deleted or altered are used in material concentration measurement detection systems, in order to carry out measurement with good precision and high sensitivity, the present invention provides a method for controlling the spatial arrangement of the energy donor and energy acceptor in the reaction complex, or the spatial arrangement of the complementation reaction donor and the complementation reaction acceptor, and a measurement system to which the method is applied.

DISCLOSURE OF INVENTION

We first labeled each of two types of materials having affinity for a subject material to be measured (materials that directly affinity bind to the subject material to be measured) with a fluorescence energy transfer-causing combination of fluorescent materials (reporters). Furthermore, reagents were prepared in which each of these materials labeled with the fluorescent materials, or each of the fluorescent materials themselves, was labeled with a leucine zipper peptide (materials for stabilizing the reporters in a spatially proximate state). These reagents and a sample were mixed, an immunocomplex was formed, and when one of the fluorescent materials was excited it was found that, due to binding based on the affinity among the materials, within the reaction complex, having weak affinity for each other, the fluorescent materials were brought in spatial proximity to each other, and a more efficient energy transfer occurred, and the present invention was thus completed.

That is, the present invention relates to a measurement method for a subject material (X) to be measured, the measurement method using a first reagent comprising a material (A) that can bond to the subject material (X) to be measured, the material (A) being labeled with a first reporter (R1), and a second reagent comprising a material (B) that can bond to the subject material (X) to be measured at a different site from that at which the material (A) bonds, the material (B) being labeled with a second reporter (R2) that causes interaction with the first reporter (R1), wherein the first reagent includes a material (C) that bonds to the first reporter (R1), the material (A) and the first reporter (R1) being directly bonded or bonded via the material (C) to form the reagent (A-R1-C or A-C-R1), wherein the second reagent includes a material (D) that bonds to the second reporter (R2) and has affinity for the material (C), the material (B) and the second reporter (R2) being directly bonded or bonded via the material (D) to form the reagent (B-R2-D or B-D-R2), and wherein the first reagent, the second reagent and the subject material to be measured form a reaction complex, and due to binding based on the affinity in the reaction complex of the material (C) of the first reagent with the material (D) of the second reagent, the first reporter (R1) and the second reporter (R2) are stabilized in a spatially proximate state, thereby causing a measurable interaction between the two reporters.

Moreover, the present invention relates to the above-mentioned measurement method wherein the subject material (X) to be measured is a material or a part thereof selected from the group consisting of proteins, peptides, antigens, antibodies, lectins, lectin-binding carbohydrates, tumor markers, cytokines, cytokine receptors, hormones, hormone receptors, cell adhesion molecules, cell adhesion molecule ligands, nucleic acids, sugar chains, and lipids; a cell; an intracellular organelle; or a low molecular weight compound.

Furthermore, the present invention relates to the above-mentioned measurement method wherein the material (A) and/or the material (B) are materials or parts thereof selected from the group consisting of proteins, peptides, antigens, antibodies, lectins, lectin-binding carbohydrates, tumor markers, cytokines, cytokine receptors, hormones, hormone receptors, cell adhesion molecules, cell adhesion molecule ligands, nucleic acids, sugar chains, and lipids; or low molecular weight compounds.

Moreover, the present invention relates to the above-mentioned measurement method wherein the material (C) and/or the material (D) are materials comprising one or two or more materials selected from the group consisting of proteins, peptides, nucleic acids, and sugar chains; or low molecular weight compounds.

Furthermore, the present invention relates to the above-mentioned measurement method wherein the first reporter (R1) and the second reporter (R2) are different fluorescent materials, and the measurable interaction between the reporters comprises a fluorescence energy transfer.

Moreover, the present invention relates to the above-mentioned measurement method wherein the first reporter (R1) is an enzyme that catalyzes bioluminescence, and the second reporter (R2) is an acceptor for non-radiative energy transfer of the bioluminescence catalyzed by the first reporter (R1).

Furthermore, the present invention relates to the above-mentioned measurement method wherein the first reporter (R1) is an enzyme that catalyzes chemiluminescence, and the second reporter (R2) is an acceptor for non-radiative energy transfer of the chemiluminescence catalyzed by the first reporter (R1).

Moreover, the present invention relates to the above-mentioned measurement method wherein the first reporter (R1) and the second reporter (R2) are molecules that form parts of an enzyme, wherein each of the first reporter (R1) and the second reporter (R2) individually has deleted or reduced enzyme activity, but the enzyme activity is generated or increased by an interaction between the first reporter (R1) and the second reporter (R2).

Furthermore, the present invention relates to the above-mentioned measurement method wherein the material (A) and the material (B) are antibodies, antibody-derived single chain Fv, Fv, a part of Fv, Fab', or Fab, or mutants thereof, each thereof recognizing different sites in the subject material (X) to be measured.

Moreover, the present invention relates to the above-mentioned measurement method wherein the material (A), the material (B), the reporter (R1), the reporter (R2), the material (C), and the material (D) comprise peptidergic materials, and the first reagent and the second reagent comprise fusion proteins.

Furthermore, the present invention relates to the above-mentioned measurement method wherein the material (C) and the material (D) are both leucine zipper peptides.

Moreover, the present invention relates to the above-mentioned measurement method wherein the measurement is carried out in a homogenous system in which the first reagent and the second reagent are made to act simultaneously on the subject material to be measured.

Furthermore, the present invention relates to the above-mentioned measurement method wherein the measurement is carried out in a heterogeneous system in which, among the first reagent and the second reagent, one of the reagents is immobilized in advance on a solid phase, and then the other reagent and the subject material to be measured are made to act on the immobilized reagent.

Moreover, the present invention relates to a measurement reagent for use in the above-mentioned measurement method, the measurement reagent including the material (A), the material (B), the reporter (R1), the reporter (R2), the material (C), and the material (D).

Furthermore, the present invention relates to a measurement kit that includes the above-mentioned measurement reagent.

'Measurement' referred to here denotes measurement of the subject material to be measured by measurement of a signal emitted by the reporter, and includes simply measuring and detecting the presence of the subject material to be measured, for example, measuring the distribution of the presence of the subject material to be measured in cells or tissue, and measuring the concentration of the subject material to be measured.

MODES FOR CARRYING OUT THE INVENTION

Figure 1:
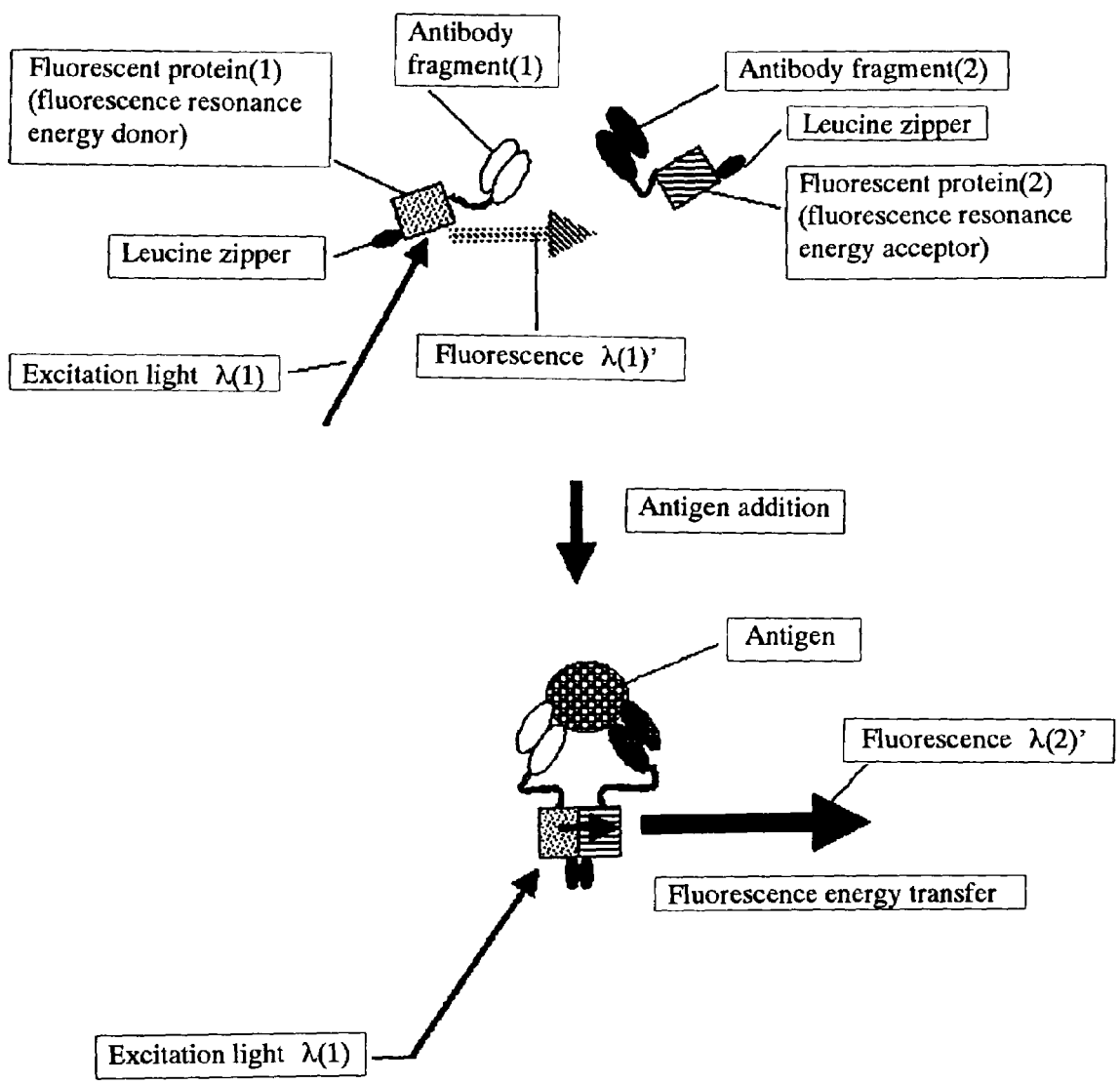
FIG. 1 shows a schematic diagram of the measurement system of the present invention.

The measurement method according to the present invention is characterized in that it uses a first reagent A-(R1-C) and a second reagent B-(R2-D), wherein further introduced to each of A-R1, which comprises a material (A) labeled with a first reporter (R1), the material (A) having affinity for a subject material (X) to be measured; and B-R2, which comprises a material (B) labeled with a second reporter (R2), the material (B) having affinity for the subject material (X) to be measured, are a material (C) and a material (D) having weak affinity for each other. The material (A) and the material (B) are able to bind to different sites of the subject material (X) to be measured.

It is desirable for the bonding between each of the materials in the first reagent A-(R1-C) to be such that the properties of each material are not lost or weakened by the other materials and, although there is no limitation in the combination of these bonds, in order for the reporters to be brought close together by the binding of the material (C) and the material (D) it is preferred that the combination is A-R1-C or A-C-R1. The same applies to the second reagent B-(R2-D).

A notation such as A-(R1-C) is conveniently used as the notation for the reagent, but the intention is to show that either of the two parts inside the parentheses are bonded to the material outside the parentheses, and unless otherwise stated represents A-R1-C and A-C-R1.

A complex (C-R1)-A:X:B-(R2-D) is formed by mixing the first reagent (C-R1)-A and the second reagent (D-R2)-B with a sample in which the measured material X is present and, moreover, as a result of the effect of increasing the local density within the complex, the material (C) and the material (D) bind together to give a more stable complex. Furthermore, even though the first reagent (C-R1)-A and the second reagent (D-R2)-B are in a bound state by virtue of the weak interaction between C and D, binding of the subject material X to be measured with the first reagent (C-R1)-A and the second reagent (D-R2)-B forms a stable complex.

Moreover, a stable complex is also formed in the same way in the case where the binding of the subject material X to be measured with the first reagent A-(R1-C) and the second reagent B-(R2-D), and the binding (C:D) between the material (C) and the material (D) occur simultaneously. As a result, the proximate state of R1 and R2 in the complex is stabilized, and a more efficient energy transfer is observed. On the other hand, when the subject material X to be measured is not present, the complex (C-R1)-A:X:B-(R2-D) is not formed, and since the interaction of C with D is weak, even if a complex A-(R1-C):(D-R2)-B is formed it is extremely unstable, and efficient energy transfer is not observed.

The subject material X to be measured in the measurement method of the present invention is not particularly limited as long as it is a material in which a material with binding capacity for the above materials is present.

With regard to this kind of subject material X to be measured, as examples thereof there can be cited peptidergic materials such as proteins and peptides, antigens, antibodies, lectins, lectin-binding carbohydrates, tumor markers, cytokines, cytokine receptors, hormones, hormone receptors, cell adhesion molecules, cell adhesion molecule ligands, nucleic acids, sugar chains, lipids, etc., or a part thereof, cells, intracellular organelles, low molecular weight compounds generally called haptens, etc.

The materials A and B that have binding capacity for the subject material to be measured in the measurement method of the present invention are not particularly limited as long as they are materials that bind specifically to the subject material to be measured, but it is necessary for them to have no affinity for each other and for each of them to recognize and bind to different parts of the subject material X to be measured. For example, in the case where the subject material to be measured is an antigen, the materials A and B could be antibodies that recognize separate epitopes. With regard to the antibodies, not only IgG obtained by the immunization of animals, but also antibody fragments such as the IgG papain digestion fragment Fab and the pepsin digestion fragment F(ab')$_2$; or Fv fragment, scFv (single chain Fv), etc., obtained by genetic engineering can be used.

With regard to the materials A and B, peptidergic materials such as proteins and peptides, antibodies, antigens, lectins, lectin-binding carbohydrates, tumor markers, cytokines, cytokine receptors, hormones, hormone receptors, cell adhesion molecules, cell adhesion molecule ligands, nucleic acids, sugar chains, and lipids, or a part thereof, or low molecular weight compounds such as haptens, etc., can also be used. Moreover, in the case where the subject material X to be measured is an antibody, a hapten that can be recognized by X can be employed as the material A, and a material that can bind to a different site of X from that where material A binds can be employed as the material B.

The first reporter (R1) and the second reporter (R2) are used as a set of reporters, and generate a measurable signal by interaction therebetween. Measurement of the subject material X to be measured in the measurement method of the present invention is carried out by measuring the signal by an appropriate measurement method.

The reporters R1 and R2 in the measurement method of the present invention are not particularly limited as long as, in the case of FRET, the combination thereof results in fluorescence energy transfer, but with regard to R1, fluorescent proteins such as GFP (Clontech) and GFP mutants, fluorescent materials such as fluorescein, etc., can be considered, and with regard to R2, fluorescent proteins such as GFP and GFP mutants, fluorescent materials such as rhodamine, etc., can be considered.

Furthermore, in the case of BRET they are not particularly limited as long as the combination thereof results in bioluminescence-fluorescence energy transfer. With regard to the reporter R1, enzymes catalyzing bioluminescence or modifications thereof can be used, and examples thereof include luminescent enzymes etc. derived from luminescent bacteria, fireflies, sea fireflies, *Pyrophorus noctilucus*, and *Renilla reniformis*. Furthermore, R1 may also be an enzyme that catalyzes chemiluminescence or a modification thereof, and a peroxidase can be cited as an example thereof. With regard to a luminescent enzyme substrate, in the case of a firefly-derived luciferase, luciferin can be cited, and in the case of a peroxidase, luminol can be cited. With regard to examples of the reporter R2, there can be cited fluorescent proteins such as GFP and GFP mutants, fluorescent materials such as rhodamine, etc.

In addition, a combination of R1 and R2 can be used wherein R1 and R2 are molecules that form parts of an enzyme and each individually has deleted or reduced enzyme activity, but wherein an interaction between R1 and R2 generates or increases the enzyme activity. As examples of this kind of reporter there can be cited the β-galactosidase Δα mutant and Δω mutant, etc.

In the present invention, the distance between the reporters R1 and R2 at which a measurable signal is generated is preferably stabilized at 0 to 50 nm, and particularly 10 nm or below.

The material C and the material D in the measurement method of the present invention are not particularly limited as long as they are materials having weak affinity for each other, and peptidergic materials such as proteins and peptides, nucleic acids, sugar chains, etc., or complexes thereof can be used. Specifically, for example, peptide fragments such as leucine zipper sequence (leucine zipper peptide) occurring in eukaryotic nuclear transcription factors such as c-Jun and c-Fos can be prepared by genetic engineering and used. In this case, mutations can be introduced into these amino acid sequences, thereby regulating the strength of the affinity. Furthermore, DNA sequences, etc. capable of complementing one another can be used. In this case, regulating the length and GC content of these DNA sequences can also regulate the strength of the affinity. Moreover, as the material C, a low molecular weight compound generally called a hapten can be employed, and as the material D an antibody or an antibody fragment that can recognize the material C can be used.

With regard to the preparation of the first reagent A-(R1-C) and the second reagent B-(R2-D) in the measurement method of the present invention, in the case where the material A (B), the reporter R1 (R2), and the material C (D) are peptidergic materials, the preparation of the reagent A-(R1-C) (B-(R2-D)) as a genetically engineered fusion protein is preferred from the point of view of the possibility of site-specific labeling and shortening the manufacturing process, but a preparation involving preparing each of the material A (B), reporter R1 (R2), and material C (D) and chemically bonding each one is also possible. Furthermore, antibody fragments can be labeled with R1 (R2), C (D), etc. via proteins such as protein G and protein A having affinity for antibody fragments, and the reagent A-(R1-C) (B-(R2-D)) can also be prepared employing an avidin-biotin interaction.

Since the measurement method of the present invention employs fluorescence energy transfer and luminescence-fluorescence energy transfer, separation of unreacted reagents A-(R1-C), B-(R2-D) is unnecessary, the washing operation that is carried out in the usual sandwich method does not have to be carried out, and since the concentration of a subject material to be measured can be measured, measurement is possible in both a homogeneous system and a heterogeneous system, but for convenience measurement in a homogeneous system is desirable.

In the case of measurement of a heterogeneous system, one of the reagents A-(R1-C) and B-(R2-D) is immobilized on a solid phase, mixed with the other reagent and a sample, and reacted for a fixed time, and measurement can then be carried out as it is or after carrying out a washing operation. With regard to the solid phase, materials such as latex particles, polystyrene beads, and ELISA microplates, which are suitably used in normal immunoassays, can be used.

The measurement system of the present invention will now be specifically explained by reference to a schematic diagram (FIG. 1), but the present invention is not limited thereto.

In the case where measurement is carried out on an antigen (X) as the subject material to be measured, two antibody fragments (1) and (2) (A, B), which bind to different sites on the antigen, are prepared. A fluorescent protein (1) (the fluorescence energy donor R1) is bonded to the antibody fragment (1), and a leucine zipper (C) is further bonded. On the other hand, a fluorescent protein (2) (the fluorescence energy acceptor R2) is bonded to the antibody fragment (2), and a leucine zipper (D) is further bonded.

Therefore, the two types of reagent (A-R1-C), which includes the antibody fragment (1), the fluorescent protein (1), and the leucine zipper, and (B-R2-D), which includes the antibody fragment (2), the fluorescent protein (2), and the leucine zipper, are used in the measurement system of FIG. 1.

By adding the antigen (X), which is the subject material to be measured, to these two types of reagent so that they are all present together, as shown in FIG. 1, a reaction complex ((C-R1)-A:X:B-(R2-D)) is formed.

When the reaction complex is formed, the fluorescent protein (1) (R1) and the fluorescent protein (2) (R2) are arranged in proximity to one another by the binding of the two leucine zippers (C, D) as a result of them affinity binding together. In FIG. 1, because the reporters are fluorescent proteins, the object of the present invention can be achieved without the necessity for binding as long as they are in proximity to one another but, according to the type of reporter, they may be also bound as necessary. In the case where the measurement system is a homogenous system, in order that a non-specific signal is not generated, it is preferable for the binding between the reporters to be weak or for there to be no binding.

As shown in FIG. 1, when the fluorescence resonance energy donor (R1) alone is irradiated with excitation light λ(1), fluorescence λ(1)' is generated. When a reaction complex such as that shown in FIG. 1 is formed, the fluorescence resonance energy donor (R1) and the fluorescence resonance energy acceptor (R2) are in proximity to one another, and fluorescence energy transfer occurs between them. Therefore, when the reaction complex is irradiated with the excitation light λ(1) fluorescence energy transfer occurs, and as a result fluorescence λ(2)' is generated.

Since the efficiency of the fluorescence energy transfer is inversely proportional to the 6th power of the distance between R1 and R2, from the point of view of a stronger fluorescence being obtained in the λ(2)' generated as a result of C and D being brought into proximity to each other than is the case where they are not brought into proximity to each other, it is suitable for high sensitivity measurement and, moreover, since R1 and R2 are always arranged at a fixed distance in the reaction complex by C and D, it is excellent from the point of obtaining a stable signal.

In this way, in the case where a fluorescent protein is used as the reporter, the fluorescence by fluorescence energy transfer gives a measurable signal, and by measuring this fluorescence, detection and concentration measurement of the subject material to be measured become possible.

The subject material to be measured is detected by measuring changes in the fluorescence spectrum attributable to fluorescence energy transfer, or changes in the fluorescence intensity ratio of λ(1)' and λ(2)'.

In the case where the concentration of the subject material to be measured is measured, a calibration curve of the fluorescence intensity ratio of λ(1)' and λ(2)' as an index is created using standard materials, and measurement is carried out by applying the fluorescence intensity ratio of λ(1)' and λ(2)' of the subject material to be measured to the calibration curve.

The present invention is explained further in detail below by means of examples, but the present invention is not limited thereby.

EXAMPLE 1

Isolation of Fluorescent Protein EYFP and ECFP DNA

For EYFP, EGFP DNA was amplified by means of PCR using Pfu DNA polymerase (Stratagene) with pEGFP (Clontech) as a template. The primers 5'-CCGCGGCCGCCATGGTGAGCAAGGGC-GAGGAGCTG-3' (SEQ ID No. 1) and 5'-CCCTCGAGCTTGTACAGCTCGTCCATGCCGAG-3' (SEQ ID No. 2) were used. The product of PCR was digested with the restriction enzymes NotI and XhoI, then separated and purified by 1% agarose gel electrophoresis, and inserted into the NotI and XhoI sites of pBluescript II KS+ (Stratagene) (pBS/EGFP). Based on this pBS/EGFP and using the following two primers 5'-CCCTCGTGACCACCTTCGGCTACGGCCT-GCAGTGCTTCGCCCGCTACCCCGACC-3' (SEQ ID No. 3) and 5'-CCACTACCTGAGCTACCAGTCCGCCCTGAG-3' (SEQ ID No. 4) site-directed mutagenesis was carried out by means of the Kunkel method (the 4 residues substituted were S65G, V68L, S72A, and T203Y) to give EYFP.

For ECFP, ECFP DNA was amplified by means of PCR using Pfu DNA polymerase with pECFP-C1 (Clontech) as a template. The primers 5'-CCGCGGCCGCCATGGTGAGCAAGGGC-GAGGAGCTG-3' (SEQ ID No. 5) and 5'-CCCTCGAGCTTGTACAGCTCGTCCATGCCGAG-3' (SEQ ID No. 6) were used.

The EYFP DNA and ECFP DNA fragments so prepared were digested by the restriction enzymes NotI and XhoI, and subjected to 1% agarose gel electrophoresis, thereby cutting out and purifying each fragment.

EXAMPLE 2

Preparation of Flexible Linker DNA

Using the two primers below and Pfu DNA polymerase, by carrying out an annealing/growth reaction a flexible linker (called 'FL4' below) DNA fragment was prepared.

The primers

5'-CCCAAGCTTTCCGGCGGGGGTGGCTCCG-GCGGGGGTGGATCCGGTGGCGGTGGCTC-3' (SEQ ID No. 7) and 5'-CCCCGCGGCCGCGCTACCGCCACCGCCG-GAGCCACCGCCACCGGAT-3' (SEQ ID No. 8) were used.

The amino acid sequence of the flexible linker so prepared was

GGGGSGGGGSGGGGSGGGGS (SEQ ID No. 9)

The flexible linker DNA fragment so prepared was digested with the restriction enzymes HindIII and NotI, and subjected to 2% agarose gel electrophoresis, thereby cutting out and purifying the fragment.

EXAMPLE 3

Cloning of Leucine Zipper Sequence from c-Jun and FosB Gene Products

E. coli HB101 containing the c-Jun and FosB gene products pJac-1 and pBSKS-FosB (Riken DNA Bank) was cultured overnight at 37° C. in 5 mL of LB broth (50 μg/mL ampicillin), and the plasmid DNA was purified by the alkaline-SDS method. Leucine zipper (called 'Lzip' below) DNA of each of the c-Jun and FosB was amplified by means of PCR using Pfu DNA polymerase with the purified plasmid DNA as a template. As primers, those below were used.

For c-Jun amplification

5'-CCCCGGATCCGTCGACGAATTCAGTGGT-TCATGACTTTCTGCTTAAGCTGTG-3' (SEQ ID No. 10),

5'-CCCCCCTCGAGGGTGGCCGGATCGCTCG-GCTAGAGG-3' (sequence No. 11);

For FosB amplification

5'-CCCCGGATCCGTCGACGAAT-TCAGTGGGCCACCAGGACAAACTC-3' (SEQ ID No. 12)

5'-CCCCCCTCGAGGGTGGCCTGACAGATC-GACTTCAGGCGG-3' (SEQ ID No. 13)

The PCR reaction liquid was purified by phenol-chloroform extraction and ethanol precipitation, and restriction enzyme digested using SalI (Takara Shuzo Co., Ltd.) and XhoI (Takara Shuzo Co., Ltd.). The restriction enzyme digestion preparations were subjected to 1% agarose gel electrophoresis, and fragments of approximately 160 bp each were cut out and purified.

It was confirmed that a base sequence determined for the cloned Lzip DNA coincided with the leucine zipper sequence described in the literature.

EXAMPLE 4

Preparation of Anti-NP (4-Hydroxy-3-Nitrophenyl-Acetyl) Antibody Expression Vector pET TRX Fusion System 32 (Novagen) was used as the fusion protein expression system.

Anti-NP (4-hydroxy-3-nitrophenyl-acetyl; abbreviated to 'NP' below) antibody ScFv DNA fragment was isolated by restriction enzyme EcoRV and HindIII digestion from pScFv (NP)AP 5.9 kbp vector (J. Biochem., 122, 322-329 (1997)). This anti-NP antibody ScFv DNA fragment was inserted into EcoRV and HindIII sites of pET32 vector (Novagen) (pET32/Trx-ScFv(NP)). The FL4 DNA fragment prepared in Example 2 was then inserted into the HindIII and NotI sites of the pET32/Trx-ScFv(NP) (pET32/Trx-ScFv(NP)-FL4).

Next, the EYFP DNA fragment and ECFP DNA fragment prepared in Example 1 were inserted into the NotI and XhoI sites of the pET32/Trx-ScFv(NP)-FL4 (pET32/Trx-ScFv(NP)-FL4-EYFP, pET32/Trx-ScFv(NP)-FL4-ECFP). Moreover, the c-Jun and FosB Lzip DNA fragments prepared in Example 3 were inserted into the XhoI sites of the pET32/Trx-ScFv(NP)-FL4-EYFP and pET32/Trx-ScFv(NP)-FL4-ECFP. The size and direction of the inserted fragments in the vectors so prepared were confirmed by restriction enzyme digestion.

The anti-NP antibody expression vectors were the four types of expression vector below.

(1) pET32/Trx-ScFv(anti-NP)-FL4-EYFP-Lzip(c-Jun)
(2) pET32/Trx-ScFv(anti-NP)-FL4-ECFP-Lzip(FosB)
(3) pET32/Trx-ScFv(anti-NP)-FL4-EYFP
(4) pET32/Trx-ScFv(anti-NP)-FL4-ECFP

EXAMPLE 5

Preparation of NP-immobilized Sepharose 4B Column

To 3 mL of EAH-Sepharose 4B (Pharmacia) was added 21 mg of NP-CAP-Osu (CRB) (dissolved in 100 μL of DMF), and it was stirred gently overnight at 4° C. The following day, the NP-immobilized Sepharose 4B was packed in a disposable column, the gel was washed with 30 mL of 0.1 M Tris buffer/100 mM NaCl (pH 7.5), then repeatedly washed alternately with 6 mL of 0.1 M acetate buffer/0.1 M NaCl (pH 4.0), 6 mL of 50 mM Tris buffer/50 mM NaCl (pH 8.0), 6 mL of 0.1 M acetate buffer/0.1 M NaCl (pH 4.0), 6 mL of 50 mM Tris buffer/50 mM NaCl (pH 8.0), 6 mL of 0.1 M acetate buffer/0.1 M NaCl (pH 4.0), and 6 mL of 50 mM Tris buffer/50 mM NaCl (pH 8.0), and finally washed with 9 mL of 0.1 M Tris buffer/0.1 M NaCl (pH 7.5).

EXAMPLE 6

Expression and Purification of Anti-NP Antibody Fusion Protein

Transformation of *E. Coli* Origami (DE3) (Novagen) was carried out using the anti-NP antibody expression vectors (1), (2), (3), and (4). The transformed clones were cultured overnight at 30° C. with shaking in 5 mL of LB broth (50 μg/mL ampicillin, 15 μg/mL kanamycin, 12.5 μg/mL tetracycline). The following day, the cultured cells were subcultured in 1.5 L of LB broth (50 μg/mL ampicillin, 15 μg/mL kanamycin, 12.5 μg/mL tetracycline: 5 L baffled flask) and culturing was continued at 30° C. When the turbidity (O.D. 600) of the culture liquid reached approximately 0.5 (approximately 6 hours of culturing), 1.5 mL of 0.1 M IPTG was added, the temperature was lowered to 16° C., and culturing was continued overnight. The following day, the cells were collected by centrifugation, 40 mL of 0.1 M phosphate buffer (pH 7.2) was added to each sample, and the cells were suspended. These cell liquids were then put through two repetitions of being kept at −80° C. and at room temperature while being shielded from light. After carrying out the freeze-thawing an ultrasonic treatment was carried out to further disrupt the cells.

The ultrasonically-treated samples were centrifuged, and the supernatants were collected. To each of the collected supernatants was added 500 μL of the NP-immobilized Sepharose 4B (Example 5), and they were gently stirred overnight at 4° C. while being shielded from light. The following day, the gels were packed in disposable column containers, and washed with a flow of 10 mL of 0.1 M Tris buffer/0.1 M NaCl (pH 7.5). Following this, 5 mL of 0.5 mg/mL NP solution (one in which it had been dissolved in 1 M Tris buffer (pH 8.0)) was added, and elution of the target protein was carried out. The eluate was collected 1 mL at a time in Eppendorf tubes. The collected samples were dialyzed against 0.1 M phosphate buffer (pH 7.2).

EXAMPLE 7

Preparation of NP-labeled Bovine Albumin

To 50 mg of bovine albumin (Sigma) dissolved in 1 mL of 0.1 M sodium bicarbonate buffer (pH 8.0) was added 14 mg of NP-CAP-Osu (CRB) (dissolved in 100 μL of DMF), and the mixture was gently stirred overnight (4° C.) while being shielded from light. The following day, the reaction liquid was put on a PD-10 column (Pharmacia) and eluted with 0.1 M phosphate buffer (pH 7.2). Since the NP is yellow, separation of the NP-labeled bovine albumin and unreacted NP-CAP-Osu on the column could be confirmed, the earlier-eluting peak was fractionated, and this was the NP-labeled bovine serum albumin. The O.D. 280 and O.D. 420 of the fractionated NP-labeled bovine serum albumin were measured by a spectrophotometer (Shimadzu Corporation), and when the NP labeling ratio of the bovine albumin was determined, the labeling ratio was NP/bovine albumin=approximately 15.

EXAMPLE 8

Measurement of NP-labeled Bovine Albumin Using Anti-NP Antibody/Fluorescent Protein/Leucine Zipper Fusion Protein Measurement of the concentration of the NP-labeled bovine serum albumin was carried out using anti-NP antibody/fluorescent protein/leucine zipper fusion protein that had been expressed by *E. Coli* Origami and purified on an NP-labeled Sepharose 4B column. Anti-NP antibody fusion proteins (Example 6) that had been affinity purified on an NP column were mixed in the combinations Trx-ScFv(anti-NP)-FL4-EYFP-Lzip(c-Jun)/Trx-ScFv(anti-NP)-FL4-ECFP-Lzip(FosB), and Trx-ScFv(anti-NP)-FL4-EYFP/Trx-ScFv(anti-NP)-FL4-ECFP, so that the concentration of each fusion antibody became 3 μg/mL, and 200 μL of each was injected into 1.5 mL Eppendorf tubes. 10 μL of NP-labeled bovine albumin (Example 7) (at bovine albumin concentrations of 0, 10, and 100 μg/mL; blank was 0.1 M phosphate buffer) was added thereto. They were then allowed to stand for one hour at room temperature while being shielded from light. After one hour, each sample was injected into the cell of a spectrofluorometer, and the fluorescence spectrum was measured.

Figure 2:
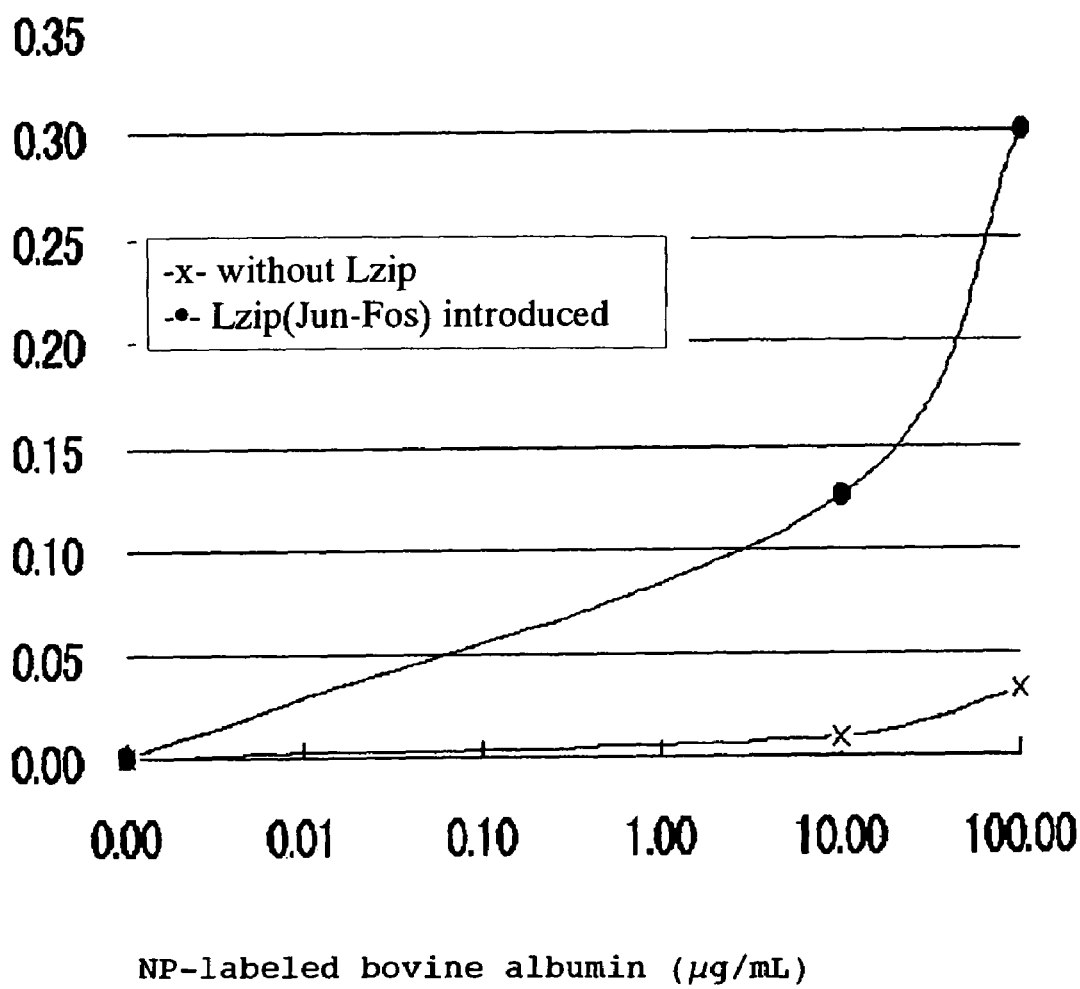
FIG. 2 shows a calibration curve for NP-labeled bovine albumin according to the measurement system of the present invention.

The fluorescence spectrum was measured (room temperature) from 450 to 600 nm using a Hitachi F2000 spectrofluorometer (Hitachi Ltd.) and exciting at 433 nm. It was found that an NP-labeled bovine albumin concentration-dependent change in the fluorescence spectrum was only observed in the case where a fusion protein into which leucine zipper had been introduced was used. When a calibration curve of added NP-labeled bovine albumin was prepared with the EYFP and ECFP fluorescence intensity ratio as the fluorescence energy transfer efficiency, as shown in FIG. 2, by introducing leucine zipper it could be confirmed that the FRET efficiency was enhanced and the measurement sensitivity was improved.

EXAMPLE 9

Extraction of Anti-human Albumin Antibody Nos. 11 and 13 mRNA and Synthesis of cDNA Culturing of a hybridoma (home-grown) secreting anti-human albumin monoclonal antibodies No. 11 and No. 13 was carried out using RPMI culture medium (Sigma) containing 10% fetal bovine serum. When the cell count reached approximately $10^7$ the cultured cells were collected by centrifugation. Extraction of mRNA from the collected hybridoma was carried out using a QuickPrep Micro mRNA Purification Kit (Pharmacia). Synthesis of cDNA was carried out using a First-Strand cDNA Synthesis Kit (Pharmacia) with 2.0 μg of the mRNA so obtained as a template.

EXAMPLE 10

Preparation of Anti-human Albumin Antibody Nos. 11 and 13 Single Chain Fv

Preparation of anti-human albumin monoclonal antibody Nos. 11 and 13 single chain Fv DNA was carried out according to the known method described in 'Antibody Engineering' (Oxford Press) with the anti-human albumin monoclonal antibody No. 11 and No. 13 cDNA (Example 9) as a template.

EXAMPLE 11

Preparation of Anti-human Albumin Antibody Expression Vector

Preparation of anti-human albumin expression vector was carried out by insertion of anti-human albumin antibody Nos. 11 and 13 ScFv (Example 10), cloned from the hybridoma-secreted anti-human albumin monoclonal antibody, into anti-NP antibody ScFv fragments cut out from anti-NP antibody expression vectors (1) to (4) (Example 4) by restriction enzyme digestion.

PCR was carried out using primers into which restriction enzyme sites (EcoRV, HindIII) had been introduced, with anti-human albumin antibody ScFv as a template. Restriction enzyme digestion (EcoRV, HindIII) of the product of the PCR was then carried out, it was subjected to 1% agarose gel electrophoresis, and the anti-human albumin antibody ScFv fragments were cut out and purified. On the other hand, restriction enzyme digestion (EcoRV, HindIII: Takara Shuzo Co., Ltd.) of pET32/Trx-ScFv(anti-NP)-FL4-EYFP-Lzip(c-Jun), pET32/Trx-ScFv(anti-NP)-FL4-ECFP-Lzip(FosB), pET32/Trx-ScFv(anti-NP)-FL4-EYFP, and pET32/Trx-ScFv(anti-NP)-FL4-ECFP prepared in Example 4 was carried out, they were subjected to 1% agarose gel electrophoresis, and vector parts other than anti-NP antibody ScFv fragments were cut out and purified. Anti-human albumin antibody expression vectors were prepared by inserting EcoRV and HindIII digested No. 11 and No. 13 antibody ScFv into the EcoRV and HindIII sites of these vectors. The size and direction of the inserted fragments in the vectors so prepared were confirmed by restriction enzyme digestion.

The anti-human albumin antibody expression vectors were the four types of expression vector below.
A) pET32/Trx-ScFv(No.13)-FL4-EYFP-Lzip(c-Jun)
B) pET32/Trx-ScFv(No.11)-FL4-ECFP-Lzip(FosB)
C) pET32/Trx-ScFv(No.13)-FL4-EYFP
D) pET32/Trx-ScFv(No.11)-FL4-ECFP

EXAMPLE 12

Preparation of Human Albumin-immobilized Sepharose 4B Column 6 g of CNBr-Sepharose4B (Pharmacia) was weighed out and washed with 1 mM hydrochloric acid (1.2 L). CNBr-Sepharose4B and human albumin (Sigma) were then mixed (0.1 M $NaHCO_3$, 0.5M NaCl pH 8.3) so that the human albumin concentration became 4 mg/mL, and gently stirred overnight at 4° C. The following day the human albumin-immobilized Sepharose 4B was washed alternately with 0.1 M acetate buffer pH 4.0 and 0.1 M Tris buffer pH 8.0.

EXAMPLE 13

Expression and Purification of Anti-human Albumin Antibody Fusion Protein

Transformation of *E. Coli* OrigamiB(DE3)pLysS (Novagen) was carried out using the anti-human albumin antibody expression vectors A, B, C, and D (Example 11). The transformed *E. Coli* was cultured in 5 mL LB broth (50 μg/mL ampicillin, 15 μg/mL kanamycin, 12.5 μg/mL tetracycline, 34 μg/mL chloramphenicol) at 30° C. overnight with shaking. The following day, the cultured cells were subcultured in 1.5 L of LB broth, and culturing was continued at 30° C. When the turbidity (O.D. 600) of the culture liquid reached approximately 0.5 (approximately 6 hours of culturing), 1.5 mL of 0.1 M IPTG was added, the temperature was lowered to 16° C., and culturing was continued overnight.

The following day, the cells were collected by centrifugation, 40 mL of 0.1 M phosphate buffer (pH 7.2) was added to each sample, and the cells were suspended. These cell liquids were then put through two repetitions of being kept at −80° C. and at room temperature while being shielded from light. After carrying out the freeze-thawing an ultrasonic treatment was carried out to further disrupt the cells.

The ultrasonically-treated samples were centrifuged, and the supernatants were collected. To each of the collected supernatants was added 500 μL of the human albumin-immobilized Sepharose 4B (Ref. Example 12), and they were gently stirred overnight at 4° C. while being shielded from light. The following day, the gels were packed in a disposable column, and washed with a flow of 20 mL of 0.1 M Tris buffer/0.5 M NaCl (pH 8.0). 2.5 mL of 0.1 M $Na_2HPO_4$ NaOH (pH 12) was then added, and elution of the target protein was carried out. The eluate was collected 500 μL at a time in Eppendorf tubes. To each of the eluate fractions was added 100 μL of 1 M Tris buffer (pH 6.5), and neutralization was effected.

EXAMPLE 14

Measurement of Human Serum Albumin Using Anti-human Albumin Antibody/Fluorescent Protein/Leucine Zipper Fusion Protein Measurement of human albumin concentration was carried out using anti-human albumin antibody/fluorescent protein/leucine zipper fusion protein that had been expressed by *E. Coli* OrigamiB(DE3)pLysS and purified with a human albumin-labeled Sepharose 4B column. Anti-human albumin antibody fusion proteins (Example 13) affinity purified with a human albumin-labeled column, in the combinations Trx-ScFv(No.11)-FL4-ECFP-Lzip(FosB)/Trx-ScFv(No.13)-FL4-EYFP-Lzip(c-Jun), and Trx-ScFv(No.11)-FL4-ECFP/Trx-ScFv(No.13)-FL4-EYFP, were mixed with 50 mM Tris buffer/50 mM NaCl/0.1% gelatin (pH 8.0) so that the concentration of each fusion antibody became 3 μg/mL, and 190 μL of each was injected into a 1.5 mL Eppendorf tube. 10 μL of human albumin (Sigma) (0, 3.1, 6.3, 12.5, 25, 50, and 100 μg/mL; diluted with 50 mM Tris buffer/50 mM NaCl/0.1% gelatin (pH 8.0)) was added thereto. They were then allowed to stand for one hour at room temperature while being shielded from light. After one hour, each sample was injected into the cell of a spectrofluorometer, and the fluorescence spectrum was measured. The fluorescence spectrum was measured (room temperature) from 450 to 600 nm using a Hitachi F2000 spectrofluorometer and exciting at 433 nm.

Figure 3:
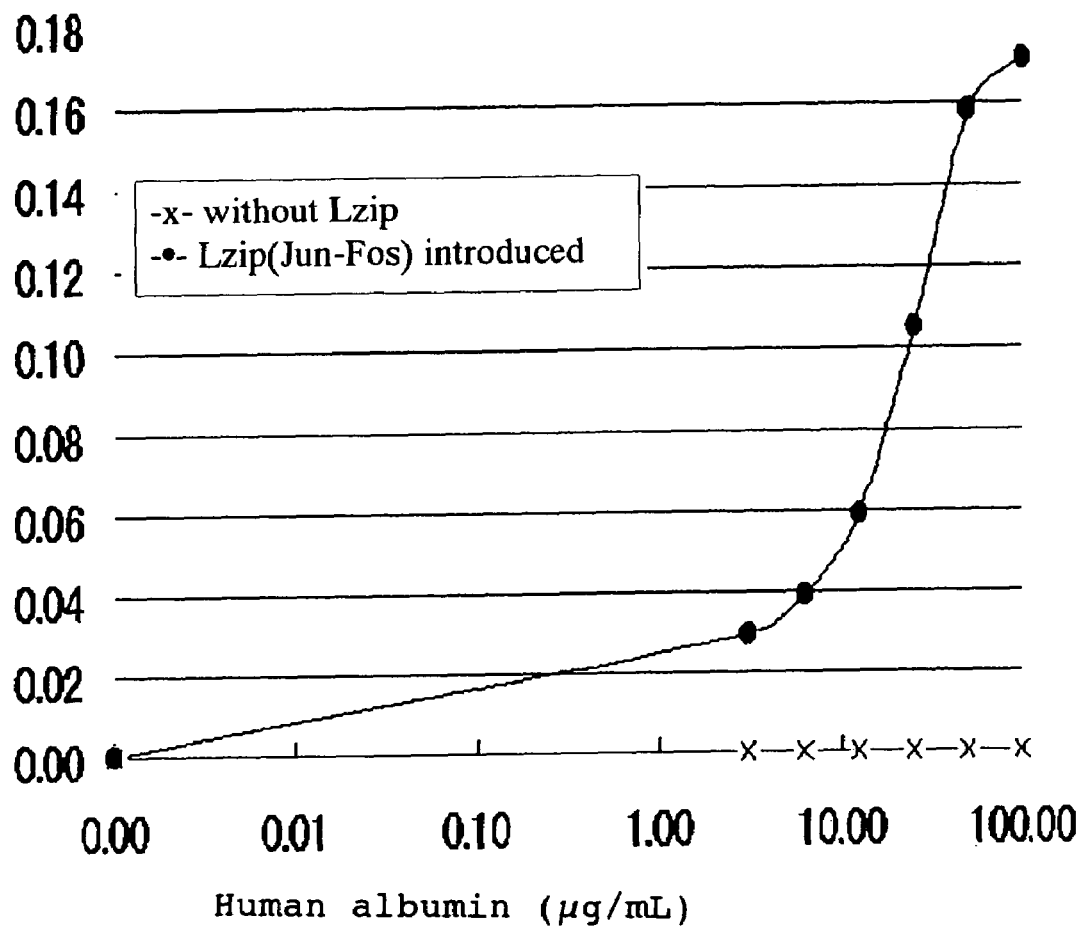
FIG. 3 shows a calibration curve for human albumin according to the measurement system of the present invention.

In the same way as with the results for NP-labeled bovine albumin, it was found that a human albumin concentration-dependent change in the fluorescence spectrum could only be observed in the case where a leucine zipper was introduced. When a calibration curve of human albumin was prepared with the EYFP and ECFP fluorescence intensity ratio as the fluorescence energy transfer efficiency, as shown in FIG. 3, as was the case where NP-labeled bovine albumin was used, with a combination of two types of monoclonal antibody, by introducing leucine zipper it could also be confirmed that the FRET efficiency was increased and the sensitivity of measurement was improved.

Industrial Applicability

In accordance with the measurement method of the present invention, efficient energy transfer can be reliably obtained, and the concentration of a material can be measured with a low background, high precision and high sensitivity. Furthermore, measurement of a homogeneous system is also possible, and in particular since a washing operation is not necessary, it is also simple to use in a clinical environment.

The invention claimed is:

1. A measurement system including a material A, a material B, a first reporter R1, a second reporter R2, a material C and a material D for use in a measurement method for a subject material X to be measured, wherein the material A, the first reporter R1 and the material C are bonded to form a reagent A-R1-C; and the material B, the second reporter R2, and the material D are bonded to form a reagent B-R2-D;

the measurement method using a first reagent comprising the material A that specifically bonds to the subject material X to be measured, the material A being labeled with the first reporter R1, and a second reagent comprising the material B that specifically bonds to the subject material X to be measured at a different site from that at which the material A bonds, the material B being labeled with the second reporter R2 that is capable of interacting with the first reporter R1, wherein the first reagent includes the material C that bonds to the first reporter R1, either the material C or the first reporter R1 being bonded to the material A to form the first reagent, wherein the second reagent includes the material D that bonds to the second reporter R2 and has affinity for the material C, the material B and the material D, or the material B and the second reporter R2 being bonded to form the second reagent, wherein the material A or the material B comprises a material or part thereof selected from the group consisting of antigen, antibody, lectin, lectin-binding carbohydrate, tumor marker, cytokine, cytokine receptor, hormone, hormone receptor, cell adhesion molecule, cell adhesion molecule ligand, nucleic acid, sugar chain, lipid, and hapten, and the material C and the material D are leucine zipper peptides, and the affinity between the material C and the material D is less than both the affinity of the subject material X for the material A and the affinity of the subject material X for the material B, wherein the first reagent, the second reagent, and the subject material X to be measured form a reaction complex, and wherein due to binding based on the affinity in the reaction complex of the material C of the first reagent with the material D of the second reagent, the first reporter R1 and the second reporter R2 are stabilized in a spatially proximate state, thereby causing a measurable interaction between the two reporters.

2. A measurement kit that includes the measurement system according to claim 1.

3. The measurement system according to claim 1, wherein the material C and material D are leucine zipper peptides selected from the group consisting of c-Jun, FosB and c-Fos.

4. The measurement system according to claim 1, wherein the subject material X to be measured is a protein or peptide.

5. The measurement system according to claim 1,
wherein the first reporter R1 and the second reporter R2 are different fluorescent materials, and the measurable interaction between the reporters comprises a fluorescence energy transfer, or wherein the first reporter R1 is an enzyme that catalyzes bioluminescence, and the second reporter R2 is an acceptor for non-radiative energy transfer of the bioluminescence catalyzed by the first reporter R1, or wherein the first reporter R1 is an enzyme that catalyzes chemiluminescence, and the second reporter R2 is an acceptor for non-radiative energy transfer of the chemiluminescence catalyzed by the first reporter R1, or wherein the first reporter R1 and the second reporter R2 are molecules that form parts of an enzyme, wherein each of the first reporter R1 and the second reporter R2 individually has deleted or reduced enzyme activity, but the enzyme activity is generated or increased by an interaction between the first reporter R1 and the second reporter R2.

6. The measurement system according to claim 5, wherein the first reporter R1 is selected from the group consisting of fluorescent proteins, fluorescent materials, luminescent enzymes derived from luminescent bacteria, fireflies, sea fireflies, *Pyrophorus noctilcus* and *Renilla reniformis*, peroxidase, beta-galactosidase delta-alpha mutant and delta-omega mutant, and the second reporter R2 is selected from the group consisting of fluorescent proteins, fluorescent materials, beta-galactosidase delta-alpha mutant and beta-galactosidase delta-omega mutant.

* * * * *

```
SEQUENCE LISTING

<160> NUMBER OF SEQ ID NOS: 13

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:Primer for
      amplifing EGFP DNA by PCR

<400> SEQUENCE: 1
ccgcggccgc catggtgagc aagggcgagg agctg                              35

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence:Primer for
      amplifing EGFP DNA by PCR

<400> SEQUENCE: 2
ccctcgagct tgtacagctc gtccatgccg ag                                 32

<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence:Primer for
      site-directed mutagenesis by Kunkel method

<400> SEQUENCE: 3
ccctcgtgac caccttcggc tacggcctgc agtgcttcgc ccgctacccc gacc         54
```

```
<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:Primer for
      site-directed mutagenesis by Kunkel method

<400> SEQUENCE: 4
ccactacctg agctaccagt ccgccctgag                                        30

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence:Primer for
      amplifing ECFP DNA by PCR

<400> SEQUENCE: 5
ccgcggccgc catggtgagc aagggcgagg agctg                                  35

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:Primer for
      amplifing ECFP DNA by PCR

<400> SEQUENCE: 6
ccctcgagct tgtacagctc gtccatgccg ag                                     32

<210> SEQ ID NO 7
<211> LENGTH: 56
<212> TYPE: DNA
<213> ORGANISM: Artificial Sequence
<220> FEATURE:
<223> OTHER INFORMATION: Description of Artificial Sequence:Primer for
      producing flexible linker DNA

<400> SEQUENCE: 7
cccaagcttt ccggcggggg tggctccggc ggggtggat ccggtggcgg tggctc            56

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence:Primer for
      producing flexible linker DNA

<400> SEQUENCE: 8
ccccgcggcc gcgctaccgc accgccgga gccaccgcca ccggat                       46

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence:Flexible
      Linker

<400> SEQUENCE: 9

Gly Gly Gly Gly Ser Gly Gly Gly Ser Gly Gly Gly Gly Ser Gly
 1               5                  10                  15

Gly Gly Gly Ser
```

-continued

```
<210> SEQ ID NO 10
<211> LENGTH: 52
<212> TYPE: DNA
<213> ORGANISM: Artificial Sequence
<220> FEATURE:
<223> OTHER INFORMATION: Description of Artificial Sequence:Primer for
      amplifing c-Jun by PCR

<400> SEQUENCE: 10
ccccggatcc gtcgacgaat tcagtggttc atgactttct gcttaagctg tg            52

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:Primer for
      amplifing c-Jun by PCT

<400> SEQUENCE: 11
cccccctcga gggtggccgg atcgctcggc tagagg                              36

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence:Primer for
      amplifing FosB by PCR

<400> SEQUENCE: 12
ccccggatcc gtcgacgaat tcagtgggcc accaggacaa actc                     44

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence:Primer for
      amplifing FosB by PCR

<400> SEQUENCE: 13
cccccctcga gggtggcctg acagatcgac ttcaggcgg                           39
```